(12) United States Patent
Nelson et al.

(10) Patent No.: US 11,090,507 B2
(45) Date of Patent: Aug. 17, 2021

(54) OPTICAL FILTER FOR SKIN TREATMENTS: HAIR ENHANCEMENT SYSTEM

(71) Applicants: William Bert Nelson, Excelsior, MN (US); Robert Sigurd Nelson, La Mesa, CA (US)

(72) Inventors: William Bert Nelson, Excelsior, MN (US); Robert Sigurd Nelson, La Mesa, CA (US)

(*) Notice: Subject to any disclaimer, the term of this patent is extended or adjusted under 35 U.S.C. 154(b) by 75 days.

(21) Appl. No.: 16/215,569

(22) Filed: Dec. 10, 2018

(65) Prior Publication Data

US 2020/0179715 A1  Jun. 11, 2020

(51) Int. Cl.

| A61N 5/00 | (2006.01) |
| A61N 5/06 | (2006.01) |
| A41D 20/00 | (2006.01) |
| A42B 1/045 | (2021.01) |
| A42B 5/00 | (2006.01) |
| A61F 9/04 | (2006.01) |
| A61F 11/14 | (2006.01) |
| A42B 1/18 | (2006.01) |
| A61N 5/067 | (2006.01) |
| A41D 31/102 | (2019.01) |

(52) U.S. Cl.
CPC .......... *A61N 5/0617* (2013.01); *A41D 20/00* (2013.01); *A42B 1/045* (2013.01); *A42B 1/18* (2013.01); *A42B 5/00* (2013.01); *A61F 9/045* (2013.01); *A61F 11/14* (2013.01); *A41D 31/102* (2019.02); *A61N 2005/067* (2013.01); *A61N 2005/0626* (2013.01); *A61N 2005/0647* (2013.01); *A61N 2005/0652* (2013.01); *A61N 2005/0657* (2013.01); *A61N 2005/0667* (2013.01)

(58) Field of Classification Search
USPC .......................................................... 607/88
See application file for complete search history.

(56) References Cited

U.S. PATENT DOCUMENTS

| 2007/0276455 | A1* | 11/2007 | Fiset | ................. | A61N 5/0617 607/91 |
| 2014/0277294 | A1* | 9/2014 | Jones | .................... | A01G 9/243 607/88 |
| 2015/0375008 | A1* | 12/2015 | Gretz | ................... | A61N 5/0618 607/90 |

* cited by examiner

*Primary Examiner* — Nicole F Lavert

(57) ABSTRACT

A wearable head article for controlling light incident on the skin, including a filter layer for allowing light to pass through over a treatment area of the head, wherein the filer layer includes material that controls the wavelengths that pass through, and a protective layer for reducing skin exposure to at least one of harmful light and non-beneficial light.

19 Claims, 5 Drawing Sheets

OPTICAL FILTER FOR SKIN TREATMENTS: HAIR ENHANCEMENT SYSTEM

TECHNICAL FIELD

The present technology relates generally to a wearable hair enhancement system to promote head hair growth, reduce hair loss, improve hair and skin health, and treat skin conditions on the head and other parts of the body.

BACKGROUND

Loss of head hair is a condition that affects many men and women. There are multiple remedies (used with varying degrees of success) for this condition including topical solution such as minoxidil, pills such as Propecia, hair transplantation, etc. More recently optical treatments using LLLR (low-level laser light) have demonstrated positive results in androgenic alopecia, including slowing and/or stopping the hair loss condition known as Carolinas, increasing follicular size, growing new hair. The laser light sources employed typically emit one or more narrow bands of electromagnetic radiation within the range of 500-1100 nm. There are multiple laser-based products commercially available "Hairmax® laser comb, laser band", "Theradome™" and "Capillus® Lasercap". Each of these products employs a number of laser diodes (up to 272 laser diodes in the Capillus® cap). Most of the vendors use continuous Laser diodes that emit at approximately 650 nm (deemed to be a beneficial wavelength) at a power per laser of 5 mW. The Capillus® 272, and Capillus Pro® provides a total output power of 1360 mW for a 6 minute session per day of wearing the cap, while the other provide less total output with durations as short as a few minutes. At least one vendor (Theradome™) uses a laser diode that emits at 678 nm (deemed to be a beneficial wavelength). The person experiencing hair loss will undergo multiple treatment sessions (individual exposure/treatment times are a function of laser intensity, the number of laser sources employed, laser wavelength(s)) involving wearing a laser hat or using a laser comb, etc. A number of published dermatology articles show the efficacy of laser treatment for hair growth and/or hair loss prevention even with variable treatment times and variable number of laser diodes used by different vendors. The natural light spectrum extends from the ultraviolet (wavelengths less than approximately 380 nm) to the infrared (greater than approximately 750 nm) and thus includes beneficial, non-beneficial and harmful wavelengths. Within the range of beneficial wavelengths specific wavelengths and wavelength bands may be preferred for treating specific medical conditions.

Preventative measures have been implemented in fabrics. Some fabrics available today are worn to prevent skin cancer. These fabrics filter out, at least partially or completely, ultraviolet (UV) radiation from the sun. Accordingly, sun-protective clothing is a more reliable, long lasting and durable protection. The SPF, UPF, etc. rated fabric absorbs and/or diffuses and/or blocks the Ultra Violet light, and typically at least much of the visible spectrum as well. However, this clothing is only a preventative for skin cancer, and limited in treating skin conditions. Conventional fabrics commonly used in clothing may also be used to block, at least in part, harmful UV radiation as well as other parts of the visible and infrared spectrum. Furthermore, reflective materials and absorbing materials can be implemented in a variety of formats such as fibers, strips, pieces of sheets, sheets, etc. (e,g, foil pieces, foil sheets, coated fabrics, coated plastic fibers, strips, pieces of sheets, sheets) can be used to block, at least in part, harmful UV radiation as well as other parts of the visible and infrared spectrum. These optical blocking/optical protective materials in the various formats described herein are collectively referred to as covering materials or covering material pieces.

SUMMARY OF THE INVENTION

In one aspect, a head article and method for controlling light incident on the skin, that may include at least one filter layer for allowing light to pass through over a treatment area of the head, wherein the filer layer includes material that controls the wavelengths that pass through, and the head article may also include a protective layer for reducing skin exposure to at least one of harmful light and non-beneficial light. Sources of light include natural sun light and man-made light. In some examples, the wearable head article may include the protective layer includes at least a UV light blocking material. As examples, the wearable head article may be a hat, a helmet, visor, bandana, scarf, headband, earphones, yarmulke, hajib, hood, mask, bonnet and any combination thereof.

In one example, the at least one filter layer may be located in at least a portion of the wearable heard article near the treatment area of the head. In another example, the at least one filter layer is at least one of an optical filter, which allows beneficial light wavelengths to pass through the optical filter, an optical converter, which converts light wavelengths into therapeutic beneficial light wavelengths, and any combination thereof. The at last one filter layer may be formed of stationary or movable optical converter materials. The filter layer optical converter material(s) employed for treating the target treatment area block wavelengths present in natural sunlight at least one of harmful and non-beneficial to the individual, including, but not limited to, UV radiation, infrared radiation, wavelengths that promote a medical condition, are cell damaging, and are not useful for treating the medical condition.

In some examples, the wearable head article may further include a liner disposed over the inner side of the wearable head article that improves air circulation, wherein the liner being formed from mesh, for allowing skin to breath. The filter layer of filter material may include, but is not limited to, one or more of a piece of rigid or flexible film, a fiber array, a piece of fabric, a reflective coating, a transmissive coating, a converter coating, an absorbing dye, a converting dye. In some examples, the wearable article may further include a band extending circumferentially around the bottom of the hat, and a brim or bill extending out from the band, wherein the brim or bill of the wearable article contains the filter layer material for treating skin conditions on the face.

In other examples, the wearable head article may include the filter layer and the protective layer being formed together in the same layer. The filter layer may be formed of light filtering film material in a panel form for inserting the panel in the wearable head article near the target treatment area. In other examples, the filter layer may be formed in a shape removably fitting into a pocket portion of the wearable head article. In other examples, the filter layer may be adhesively bonded to the wearable article. In yet other examples, the filter layer is a plurality of panels forming a grid portion of the wearable head article for controlling the light at the target treatment area of the head.

Further, the wearable head article may include electronics. In one example, the wearable head article may include at least one sensor that monitors for at least one of temperature, light, and wavelength of light. The wearable head article may further include light means that are attached to an inner side of the wearable head article in an array for emitting beneficial light within a treatment wavelength range. In another example, the wearable head article may include a control controlling an array of lights attached to a wearable head article for treating skin conditions. The control may include a programmable control means for controlling delivery of power to the array of lights, wherein the array of lights are located on an inner side of a filter layer, which allows a wearable head article for controlling light incident on the skin, including light to pass through over a treatment area of the head, wherein the filer layer includes material that controls the wavelengths that pass through. In some examples, the programmable control means further controls one or more of timing of power delivery to the array, duration of power delivery, strength of power delivery, power, delivery of power to a portion of the array of lights, a light wavelength for treatment, emitting light from the array at certain points targeting an area of the skin for treatment, receiving signals from at least one sensor, and other controls means. One or more means can be employed to power the electronics including, but not limited to, batteries, capacitors, solar converters, mechanical-to-electrical converters, external electrical power sources.

In one example, the invention may include a method for treating skin conditions including providing a wearable head article for controlling light on the skin, and blocking wavelengths with a filter layer by allowing wavelengths of light in a treatment range for treating skin conditions to pass through over a treatment area of the head. The filer layer includes material that passes light waves within a wavelength treatment range to pass through the filter layer over a treatment area of the skin; and protecting skin with a protective layer for reducing skin exposure to at least one of harmful light and non-beneficial light.

Various medical skin conditions may be treated by means of variable phototherapy using one or more beneficial selective wavelengths or wavelength bands present in photonic sources such as natural sunlight, converted sunlight and artificial optical sources. Natural sunlight can be filtered to preferentially transmit beneficial wavelengths for treating medical conditions by means of stationary or moveable optical filter materials (which may have fixed or tunable optical filter properties). Stationary or movable optical converter materials (conversion filters) can be employed to convert harmful and/or non-beneficial (and less-beneficial) radiation present in natural sunlight to beneficial wavelengths for treating medical conditions. Programmable, stationary or movable (beneficial) artificial optical sources can be employed for treating medical conditions. Selective regions of the human body can be treated. Optical filter means, optical converter filter means and artificial optical source means can be incorporated into wearable articles of clothing, wearable structures and external structures used to regulate, and in some examples, control natural sunlight.

Wearable head articles, such as hats, may have different materials to achieve the best treatment for specific skin conditions. For example, optical filter material(s) and/or optical converter (filter) material(s) employed may provide additional benefit to the user by reducing the transmission of wavelengths present in natural sunlight deemed to be harmful to the individual (e.g. UV radiation, wavelengths that promote a medical condition) and/or are not useful for treating the medical condition (e.g. infrared radiation).

In other examples, other devices may regulate treatment, as well as protect the user from harm. In one example, timers and/or electronic monitors can be employed to warn the user of excessive exposure conditions to one or more areas of skin that are to be treated as well as reporting general exposure/health conditions (e.g. pulse, temperature, breathing).

The example of this disclosure is wearable head articles, however, the disclosure may also be considered for wearable articles of clothing and wearable structures. Wearable articles of clothing that may utilize this disclosure include, but are not limited to, head coverings/head gear (e.g. hats of any type or style, visors, hoods, head bands, bandannas, scarfs, masks, bonnets, helmets (e.g. bike, skate board, racket ball, football, baseball, ski, motorcycle/race car, construction, military), costumes, neck ties, collars, necklaces, bracelets, sports equipment (e.g. elastic wrap, towels, exercise boots), belts, pants, shorts, dresses, jackets, gloves, socks, footwear of any type or style and blankets. Wearable structures may include, but are not limited to, military/video game equipment (helmets, goggles, gloves, pads, armour, boots), a back pack, a heart monitor and head phones.

External structures used to regulate natural sunlight include, but are not limited to, umbrellas/parasols, cabanas, tents, deck coverings (awnings), green houses, building sunroofs, building windows, vehicle sunroofs, vehicle windshields, vehicle windows, airplane windshields and airplane windows.

Medical conditions that can be treated using this invention include, but are not limited to, hair loss, psoriasis, fungus, acne, rosacea, wrinkles/aging, capillaries, bruising, sunburns, bacterial infections, insomnia and depression. The disclosure may also be used for improving the esthetic appearance of the skin, including but not limited collagen support and growth, and cellular rejuvenation and regeneration. Other conditions that respond or improve to light exposure may also be considered.

It will be appreciated that reference herein to "preferred" or "preferably" is intended as exemplary only. Throughout the description, examples are given as illustrative and are not limited as to the only means possible. The details of one or more examples are set forth in the accompanying drawings and the description below. Other features and/or advantages will be apparent from the description and drawings, and from the claims.

The articles "a" and "an" are used herein to refer to one or to more than one (i.e., to at least one) of the grammatical object of the article. By way of example, "an element" means one element or more than one element. As used herein, the use of the singular includes the plural (and vice versa) unless specifically stated otherwise. Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present.

DETAILED DESCRIPTION

In general, this disclosure is directed to techniques that may enable the treatment of one or more medical conditions by means of variable phototherapy using one or more beneficial selective wavelengths or wavelength bands provided by at least one of natural sunlight (sunlight), artificial illumination means such as artificial optical sources, converted sunlight. The natural sunlight spectrum can be filtered to preferentially transmit beneficial wavelengths for treating medical conditions by means of stationary or moveable pieces of optical filter materials (which may have fixed or tunable optical filter properties). Stationary or movable pieces of optical converter materials (optical converter filter materials), including pieces coated with wavelength shifters (converters), can be employed to convert a part of the natural sunlight spectrum to beneficial wavelengths for treating medical conditions. Directly and/or remotely programmable artificial optical sources emitting beneficial wavelengths of light, either stationary or movable, can be employed for treating medical conditions. The power of artificial illumination means such as artificial optical sources can be controlled in order to provide appropriate levels of treatment as needed. Selective regions of the human body can be treated. Optical filter means, optical converter filter means and artificial illumination means (including implementations that combine at least two of optical filter means, optical converter filter means and artificial illumination means can be incorporated into any of a wearable article of clothing, a wearable structure and an external structure. Optionally, optical converter filter means and optical filter means can be combined into a single piece of material. Alignment of clothing, wearable structures and external structures with the regions of the body to be treated can be done by direct visual means, remote visual means (e.g. a video camera) and physical touch.

Furthermore, optical filter material(s) as well as optical conversion filters can be employed that benefit the individual by reducing or significantly reducing the transmission of wavelengths present in natural sunlight and/or artificial illumination means deemed to be harmful to the individual (e.g. UV radiation, wavelengths and wavelength bands that promote an undesirable medical condition). In addition, optical filter material(s) can be employed that reduce or significantly reduce transmission of wavelengths in natural sunlight and/or artificial illumination means that are of no benefit in treating the medical condition (e.g. infrared radiation contributes to unwanted heating). Optical filler materials and optical converter filter materials can be employed that reduce the transmission of wavelength bands within the natural sunlight and/or artificial illumination means spectrum deemed to be harmful and/or of no benefit in treating the medical condition.

Figure 1:
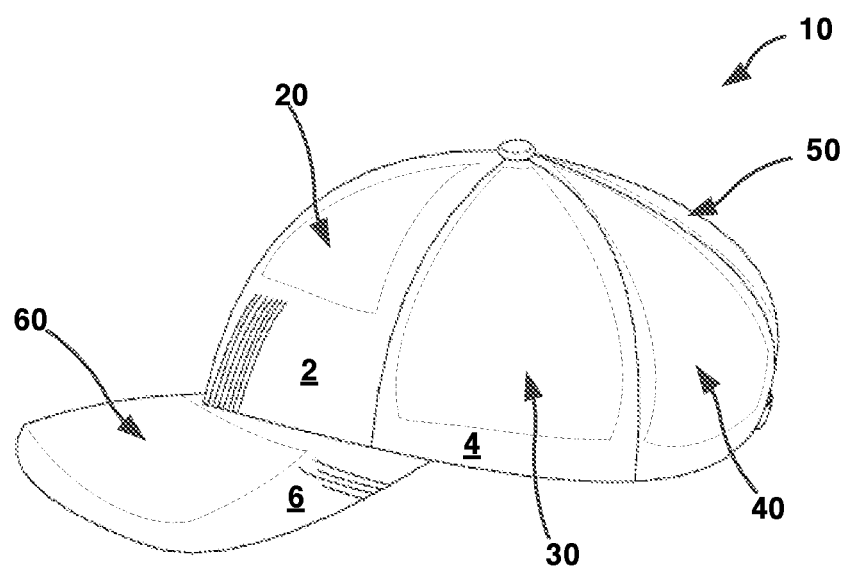
FIG. 1 is a conceptual diagram illustrating a perspective view of an optical filter means incorporated into wearable article head gear, in accordance with one or more aspects of the present disclosure.

FIG. 1 is an example of a wearable head article 10 or controlling light incident on the skin. In the example, the wearable head article 10 is a baseball hat, including a filter layer for allowing light to pass through over a treatment area of the head. The consumption of beneficial foods or medicines as well as the application of beneficial medicines topically may alter the preferred band or bands of treatment wavelengths employed without the use of these foods and/or medicines. Thus, the preferred or acceptable band or bands of wavelengths employed for treating a specific individual are adapted to suit the needs of that individual. The filer layer includes material that controls the wavelengths that pass through and a protective layer for reducing skin exposure to at least one of harmful light and non-beneficial light.

FIG. 1 is an example of a conceptual diagram illustrating a filtering baseball hat 10 with a filter layer (e.g. 20, 30, 40, 50, 60) in the panels of baseball hat 10 that allow light to pass through the filter layer (e.g. 20, 30, 40, 50, 60) over a treatment area of the head. In the example of FIG. 1, visor filter layer 60 may allow light to pass through to treat acne on the face of the hat wearer. In another example of FIG. 1, forehead filter layer 20 may be on baseball hat 10 in the front portion of the hat that is nearest to the forehead. Thus, when sunlight shines on baseball hat 10, the rays of the light may go through the material of a forehead portion 2 of the baseball hat. Some of the light rays may become absorbed, filtered or deflected from material of forehead portion 2, of baseball hat 10. In other examples, forehead filter layer 20 may be an insert of different filter material that is different from the material of baseball hat 10. Forehead filter layer 20 may be approximately the same size of forehead portion 2 of baseball hat 10, so that forehead filter layer 20 fills the entire area of the forehead portion 2. In other examples, any portion of forehead portion 2 may include forehead filter layer 20, allowing beneficial light wavelengths to reach a target skin treatment area below the surface of baseball hat 10 at forehead filter layer 20. In this example, forehead filter layer 20, or generally any filter layer, may be in at least a part of the area of forehead portion 2, and be any size. In other words, any size is possible for forehead filter layer 20, so that beneficial light wavelengths reach the target skin treatment area on the skin inside baseball hat 10.

In another example, for treating skin conditions of the back of the head such as the baseball cap wearer has a receding hairline in the back crown of the head, other filter layer locations may include locations or portions of baseball had 10 that are nearest to the area of the skin targeted for treatment. For example, a side filter layer 30 and a back-filter layer 40 may transmit light wavelengths that are advantageous for improving hair growth on the scalp. Side filter layer 30 and back filter layer 40 may transmit advantageous wavelengths by absorbing wavelengths that are not in the beneficial range of wavelengths for hair growth. In another example, none beneficial wavelengths for hair growth may be reflected or deflected off of side filter layer 30 and back filter layer 40.

In another example, for treating skin conditions of the left crown or left side of the wearer's head, baseball hat 10 may include a left filter layer. The left side, such as side filter layer 30, of baseball hat 10 may be nearest to a skin condition on the wearer's left temple or scalp. Proximal locations to target skin treatment areas may increase the level of beneficial light that the target area receives, and by increasing the light in a beneficial wavelength range, the health or condition of the skin in the target skin treatment area may improve.

Baseball hat 10 of FIG. 1 may also include a protective layer includes at least a UV light blocking material. The material may be coated, bonded, woven, or made with the material of any of the filter layers (e.g. 20, 30, 40, 50, 60) of FIG. 1, or the blocking material may be a separate material and formed in a separated layer of baseball hat 10. For example, front panel 2 may be made of a UV blocking material, and forehead filter layer 20 may a separate layer that inserts as a film layer into the front panel of baseball hat 10. In this example, the layers are completely separate. In another example, forehead filter layer 20 may be infused with, a coating of, interwoven with, etc. front panel 2 that is made of a UV blocking material. In another example, filter layer 20 may contain pieces of protective UV blocking material, that may filter out the harmful UV rays. In yet another example, the UV blocking material may be the same as the hat material, mix together or interwoven, or it may be a chemically bonded, coated, and/or attached to forehead filter layer 20 material.

In the example of FIG. 1, the wearable head article is a baseball hat. However, the disclosure may be used with any type of a hat, a helmet, visor, bandana, scarf, headband, earphones, yarmulke, a hajib, hood, mask, bonnet and any combination thereof. Any type of head equipment or clothing may include the features of the disclosure to beneficially treat skin conditions of the skin of the head.

Throughout this disclosure, the example of a baseball hat is given. However, this disclosure includes using filter layers for controlling light with any wearable article of clothing. Generally, articles of clothing may be any article worn on the body. Examples of articles of clothing may include, but are not limited to, head coverings/head gear (e.g. hats of any type or style, visors, hoods, head coverings, caps of any kind, shower caps, head bands, bandannas, scarfs, masks, bonnets, helmets (bike, skate board, racket ball, football, baseball, ski, motorcycle/race car, construction, military), costumes, neck ties, collars, necklaces, bracelets, sports equipment (e.g. elastic wrap, towels, exercise boots), belts, pants, shorts, dresses, leotards, martial arts uniforms, uniforms, jackets, gloves, socks, footwear of any type or style. It may also encompass blankets and wearable coverings for warmth.

In addition to wearable articles of clothing, this disclosure may also be used with wearable structures include, but are not limited to, military/video game equipment (helmets, goggles, gloves, pads, armor, boots), a back pack, a heart monitor and head phones. In other examples, external structures may use the aspects of this disclosure. External structures may include, but are not limited to, hand fans, sun shades, umbrellas/parasols, cabanas, tents, deck coverings (awnings), green houses, building sunroofs, building windows, vehicle sunroofs, vehicle windshields, vehicle windows, airplane windshields and airplane windows.

Medical conditions that can be treated using this invention include, but are not limited to, hair loss, psoriasis, foot fungus, acne and depression.

One embodiment of the present invention makes use of natural sunlight to promote hair growth in general and more specifically to promote head hair growth and/or prevent/reduce head hair loss. (Other conditions may also be treated.) Harmful radiation present in natural sunlight (including radiation in the UV range) to the scalp/dermis is attenuated/blocked to a significant degree while allowing beneficial natural sunlight wavelengths and/or bands of wavelengths to pass through a head covering (head gear) including, but not limited to, a cap, a hat, a shower cap, a helmet, a scarf, a mask, a bonnet, and a band. The head covering incorporates an open grid structure that permits one or more pieces of optical filter material (and/or optical conversion filter material) to be mounted over a region of the head to be treated in order to encourage hair growth. Covering materials (e.g. optical protective materials such as pieces of treated cloth, pieces of reflective materials used for optical blocking, etc.) can be mounted on one or more of the remaining open areas of the grid structure that substantially block (at least) harmful radiation. In one implementation the remaining open areas of the grid are left open. In one implementation the head gear incorporates at least one of fixed or adjustable perforations, holes, slits and a fan(s) in order to encourage air circulation. In another implementation the head gear incorporates or includes separating structures to displace hair that would otherwise partially-shade the area to be treated. Optionally, wavelengths deemed to be of limited or no benefit can be reduced or significantly attenuated/blocked by the optical filter material pieces and/or the covering materials (also referred to as covering material pieces or covering pieces).

The optical filter materials pieces with fixed or tunable (bandpass) properties employed to promote hair growth can be mounted in the head covering/head gear in stationary positions (location, orientation angle) which can be changed as treatment progresses.

Alternatively, the optical filter material pieces may have adjustable mounts that permit the angular orientation and/or location to be modified manually or by motor control so as to improve the effectiveness of hair growth treatment over a specific area of the scalp. The motor controller can be integrated into the hat and/or linked to a remote control device (e.g. a dedicated wired or wireless remote controller, a cell phone, a cell phone with a camera, a smart watch, a tablet such as an iPad, a fixed or portable computer, a Television, a camera).

The optical filter materials (pieces) employed can be rigid or flexible, flat or curved and in the form of smooth or structured sheets, pieces of sheets (including geometric shapes and irregular shapes), strips, fibers. Preferably the optical filter materials employed add relatively little to the weight of the head covering/head gear. The thickness of the optical filter materials employed is typically less than a few millimeters, including a substrate (if present).

The optical filter materials pieces with fixed or tunable (bandpass) properties employed to promote hair growth can be mounted in the head covering/head gear in stationary positions (location, orientation angle) which can be changed as treatment progresses. Alternatively, the optical filter material pieces may have adjustable mounts that permit the angular orientation and/or location to be modified manually or by motor control so as to improve the effectiveness of hair growth treatment over a specific area of the scalp. The motor controller can be integrated into the hat and/or linked to a remote-control device (e.g. a dedicated wired or wireless remote controller, a cell phone, a cell phone with a camera, a smart watch, a tablet such as an iPad, a fixed or portable computer, a Television, a camera).

In some examples, structured optical filter materials (and structured optical converter filter materials) implement patterned or irregular surfaces (or incorporate internal structures) to improve the overall collection efficiency of beneficial light and/or the distribution of beneficial light over the skin surface to be treated. For example, collection efficiency can be improved by reducing the angular dependence on transmission of the incident beneficial light. Holographic and Fresnel structures have been used to increase light collection efficiency for a non-directional source such as the sun (the directionality and spectral distribution of sun light changes with position in the sky). Other surface patterns include, but are not limited to, patterns of horn (concentrator) structures, corrugated structures, groove structures, dimple structures, roughened surface structures.

The head covering/head gear can be adjustable and include an internal frame that can allow any of perforations, holes, slits, apertures (windows) to be fixed or moveable (allowing selective positioning) to enhance treatment of specific areas on the head. The head covering/head gear can have separating structures that are fixed or can be selectively positioned such as dimples, short optical fibers, etc. on the internal surface or mounted to the frame of the head covering/head gear in order to separate hair so as to promote photo stimulation of the dermis in those areas in which the separating structures are present. The head covering/head gear can include a brim or brow. The brim or brow can incorporate optical filter materials that preferentially transmit one or more beneficial wavelengths or wavelength bands while preferentially filtering out harmful radiation in order to treat skin conditions such as acne.

The principle of treating ailments such as hair loss and acne by controlling the solar irradiance properties incident on a specific area of the body can be applied to additional articles of clothing including, but not limited to, shirts, pants, dresses, foot wear, athletic wear (including swim wear and swim caps, elastic wrap, towels, exercise boots), etc. Furthermore, this principle can be applied to wearable structures include, but are not limited to, video game equipment (helmets, goggles, gloves, pads, armor, boots, gloves) and head phones as well as non-clothing items (external structures) wherein individuals may benefit from controlling the solar irradiance properties incident on one or more areas of the body. For example, a car sun roof (including a convertible roof) or an area thereof as well as car windows can implement transmission over a preferred bandwidth to promote hair growth or treat acne. Similarly, this principle can be implemented with one or more windows or in a tent, a home, a spa, a store, a building, a sun deck, a home or building roof top, etc. as well as sun umbrellas, sun sails, patio covers, etc.

Currently, the preferred range of beneficial natural sunlight wavelengths for hair growth and/or maintenance is presumed to extend from approximately 550-1,100 nm although the degree of benefit (for a specific medical condition) need not be uniform across this broad spectral band. (For example, narrow band lasers within this wavelength range have been employed to promote hair growth.) Therefore, this range of wavelengths or one or more wavelengths and/or wavelength bands within this range may be selectively employed using appropriate fixed and/or tunable optical filter (and/or optical conversion filters). Furthermore, the preferred wavelength range for treating one or more types of skin acne includes at least 400-420 nm (this range may be expanded by the use of optical conversion filters). The preferred range of beneficial natural sunlight wavelengths may be modified as new scientific evidence and/or new treatment techniques (including new foods as well as new topical and/or oral medicines for treating hair loss, skin acne, etc.) become available and therefor the spectral transmissive properties of the fixed or tunable optical filters (as well as spectral properties of optical conversion filters and artificial beneficial optical sources) employed may be modified accordingly.

The light wavelengths may be controlled or filtered, because the wavelength separation between beneficial to harmful or not beneficial is not that great. For example, light that kills bacteria has a wavelength range of 185-254 nm, but harmful light causing cellular disruption has a wavelength range of 260-270 nm.

Just a few examples of the multiple conditions that benefit from certain ranges of light wavelengths are as follows:

| | |
|---|---|
| Hair treatment laser/infrared | 600 nm-800 nm |
| Acne | 400 nm-500 nm |
| Alopecia | 600 nm-700 nm |
| Fungus | 980 nm-1300 nm |
| Depression | 450 nm-620 nm |
| Vitiligo | 300 nm-400 nm |
| Wound healing | 620 nm-700 nm |
| Jaundice | 350 nm-550 nm |
| Sleep | 450 nm-480 nm |
| Psoriasis | 280 nm-400 nm |

Alternatively, the hat/head covering/head gear can be made of a semitransparent cloth that is treated with UV blocking or other wave length coatings so that selective wavelengths that promote health are allowed through. A cloth that is currently used for shirts that is semi-transparent and has a sun block applied would be an example.

Figure 2:
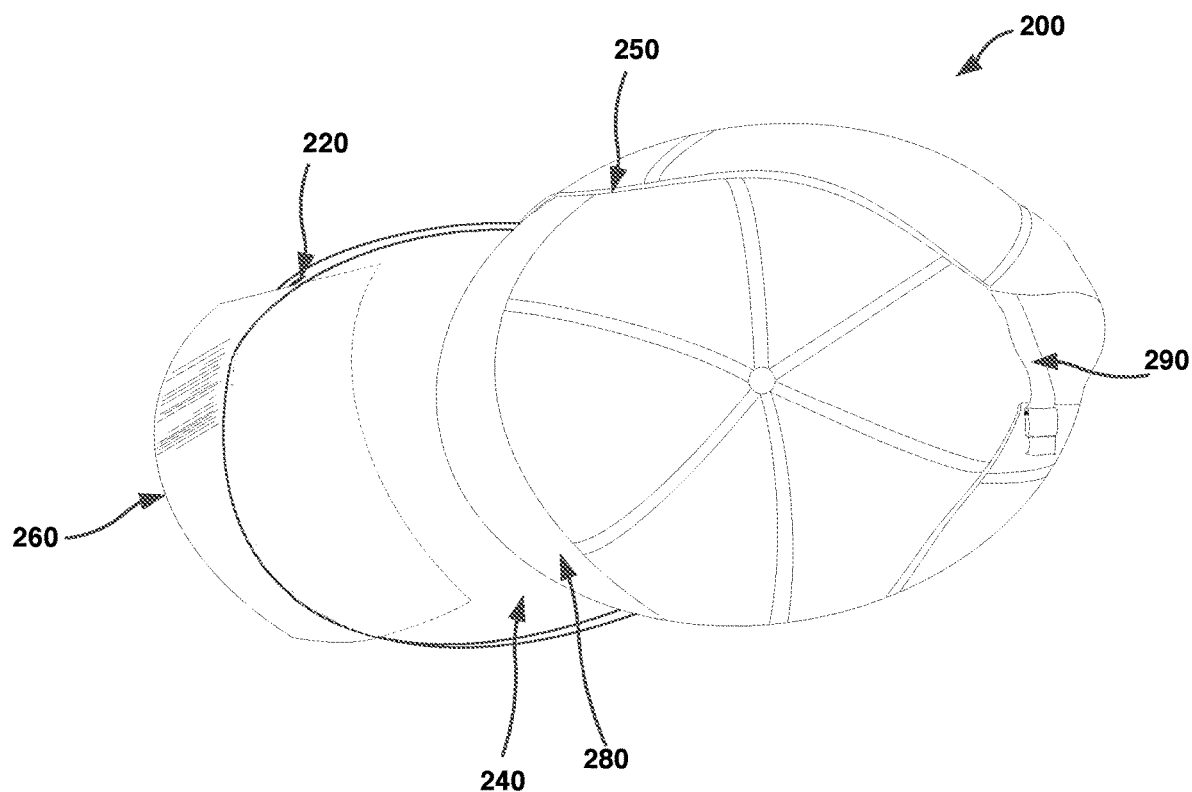
FIG. 2 is a conceptual diagram illustrating a perspective view of layers of an optical converter means incorporated into a wearable article head gear, in accordance with one or more aspects of the present disclosure.

In another example not illustrated in FIG. 2, the hat/head gear may include a face panel that extends from the bottom of the front of the cap downward. The face panel may be a hood or shield of stiffer material that allows a more targeted treatment of the face, neck ears, and upper chest area. The face panel may be flat, curved for form over the face, or shaped to shine light and improve targeted treatment. The face panel may extend from, for example, band 280 (of FIG. 2) and extend downward any length from 1 inch to 18 inches, or more depending on the location of the target treatment area. The face panel may be attached, so that the face panel extends parallel to the face during treatment. In some examples, the face panel may be attached to the hat/head gear so that it has limited or no motion. In other examples, the face panel may be attached to the hat/head gear with a hinge or moveable connecter, allowing the face panel angle with the face of the patient (or target treatment area) to be adjusted for optimal treatment. In another example, the face panel may attach with Velcro, a zipper, a snap, etc. and may be removeable.

Figure 4:
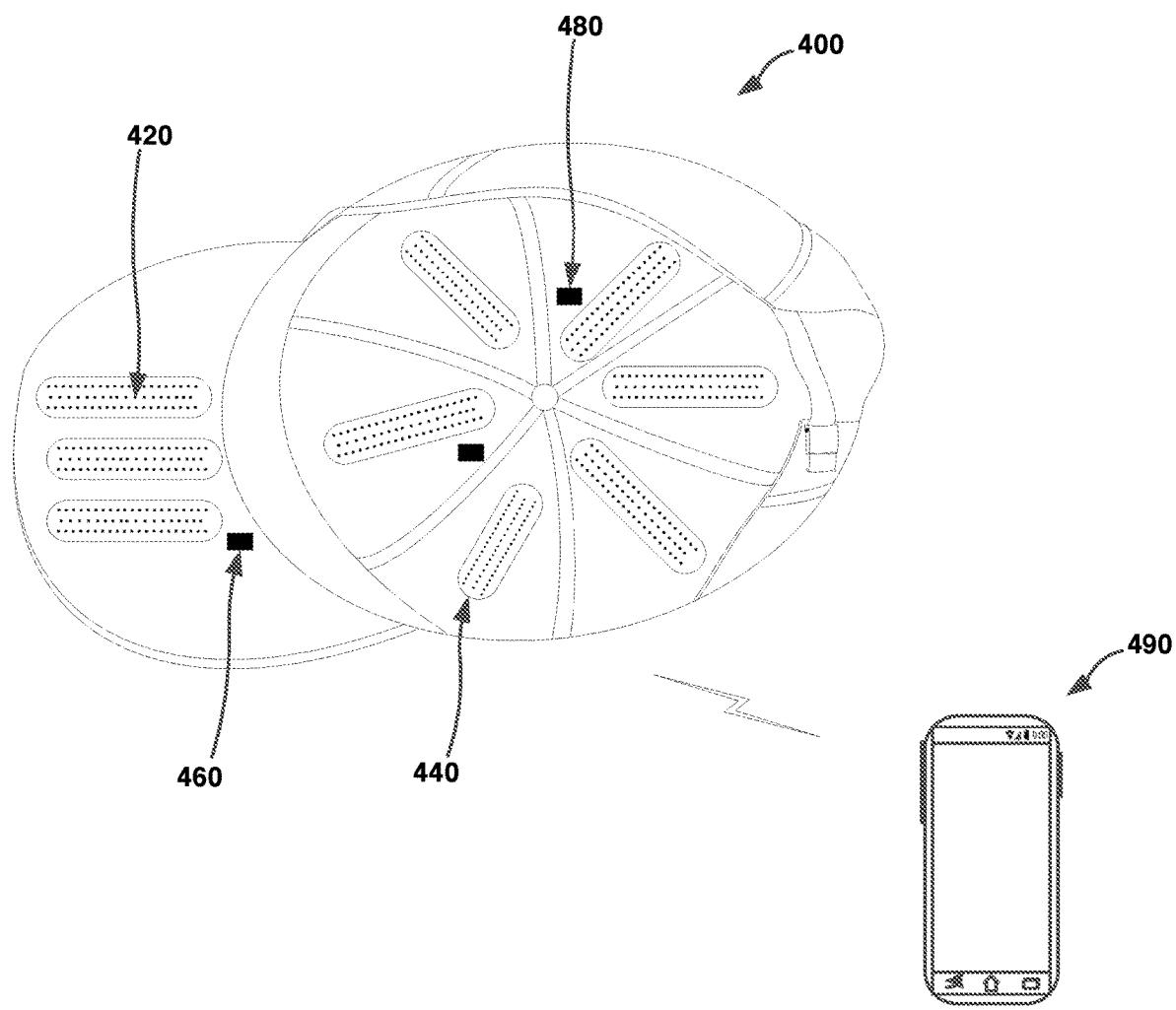
FIG. 4 is a conceptual diagram illustrating a perspective view of an artificial optical source means incorporated into a wearable article head gear, in accordance with one or more aspects of the present disclosure.

The face panel may be clear, translucent or opaque, and it may include an array of treatment light (such as bill lights 420 of FIG. 4). In some examples, the patient may be able to wear the face panel and see through it, so that the user is more comfortable and does not need to remove it to see. The face panel may be made of the filter layer material, so that it may filter the light through the face panel as described herein. The inner side of the face panel near the face may contain the artificial light source so that it shines toward the face. The artificial light source may be anywhere on the inner side of the face panel, so that the artificial lights may target any portion of the upper chest, ears, face or neck for treatment.

Throughout this disclosure, several exemplary embodiments are described based on either a device or apparatus, or a method. However, one skilled in the art would be able to implement the invention in at least one of method, system, and device or apparatus product.

FIG. 2 is an example of an illustration of the wearable head article, i.e. a baseball hat 200, showing a filter layer 260 material as a separate material, being inserted into an insert opening 220 of baseball hat 200. However, the material of filter layer 260 is formed of stationary or movable optical converter materials. For example, filter layer 260 could be flexible, so that bending is possible improving ease of placing filter layer 260 into baseball hat 200. Movability, or flexibility, may allow the flexible film shape of filter layer 260 formed in a shape removably fitting into a pocket portion of the wearable head article at insert opening 220. Insert opening 220 may be a slit or recess of layers that filter layer 260 may fit into for placement.

Filter layer 260 of the wearable head article may be made of filter material with certain properties. For example, the material may include a piece of flexible film. The piece of film may be made of insert materials for filtering light waves in a specific light wave range length. The flexible nature of the material may also allow the film to not only insert fully into baseball hat 200, but also to reduce the appearance or noticeability of the film, e.g., filter layer 260, within the material of the wearable head article. The flexible material may also improve comfort while wearing the article and conform better to the shape of the wearer's head. Different levels of flexibility are possible by reducing the rigidity of the material enough but maintaining the structural integrity of the film, so that it does not tear or fold when inserting it into baseball hat 200.

In another example of the wearable article, baseball hat 200 may also include a band 280 extending circumferentially around the bottom of the hat. Band 280 may be a seam of baseball hat 200, or in another example, band 280 may be a seam cover at the lower edge of baseball hat 200 and covering the seam that runs along a bottom edge 250 of baseball hat 200. Bottom edge of baseball hat 200 runs circumferentially around, creating a recessed opening for receiving the wearer's head. In some examples, wearable head articles may include features such as bills, brims, securing, tightening, or fitting mechanisms at or near the band. At the front portion of baseball hat 200, a brim may extend from or near bottom edge 250. In some examples, the brim may extend at the seam of baseball hat 200. At this portion, baseball hat 200 may include a brim or bill 240 extending out from band 280, seam, or other area strong enough to support the brim. Bill 240 may be made of the same material as baseball hat 200, or may include other materials, such as cardboard or other stiff material that may more rigidly extend from baseball hat 200. In some examples, bill 240 of the wearable article may contain the filter layer material for treating skin conditions on the face. The brim filter layer 260 may be in addition to another filter layer film in baseball hat 200, for example forehead filter layer 20 of forehead portion 2, of FIG. 1.

In the example of FIG. 2, the wearable head article of claim 1, filter layer 260 may be an optical filter that is formed of a light filtering film material in a panel form for inserting the panel in the wearable head article near the target treatment area. In some examples, optical filter materials may include, but are not limited to, plastics, glasses, laminates, thin film structures and sprays applied to plastic or glass, color plastic or glass filters, polarizing filters. Plastics and glasses (including plastics and glasses with structured surfaces or internal structures) may be impregnated or coated with any of absorptive, reflective, polarizing and converting materials. Untreated plastic or glass materials can function as effective UV absorbers over most or all of the UV range (e.g. polycarbonates, acrylics, special UV absorbing acrylics). Examples of common optical filters include the protective lens filters that can be attached to a camera lens, polaroid lens filters attached to vision glasses, etc. Commercial solar control multilayer coatings (bandpass filters) have been developed that reduce the transmission (often by reflection) of infra-red light while filtering out UV radiation (e.g. the 3M Prestige series). Converting materials (wavelength-shifters) are used to enhance the intensity of beneficial light wavelengths by absorbing shorter wavelengths and re-emitting light at longer wavelengths (at least in part within the range of beneficial wavelengths). The properties of the optical thin film may be controlled by an electric field (products are commercially-available for light control in car windows, office buildings, planes windows, etc. such as Research Frontiers' SPD-SmartGlass technology). Optionally, optical converter filter material pieces can be employed with optical filter material pieces or in place of optical filter material pieces.

In other examples, materials may be coated or treated for optical filter effect. In some examples, filter layer 260 may be impregnated with dyes or carbon particles or coated with a layer of vapor deposited metal to accomplish the desired filtering result of filtering wavelengths of a pre-selected range. Metallic coatings, for example aluminum, reflect incident light, thereby reducing the transmission of UV and visible light. However, other metals, dyes, and other materials may be added to achieve the desired filtering effect of certain wavelength ranges.

Figure 3:
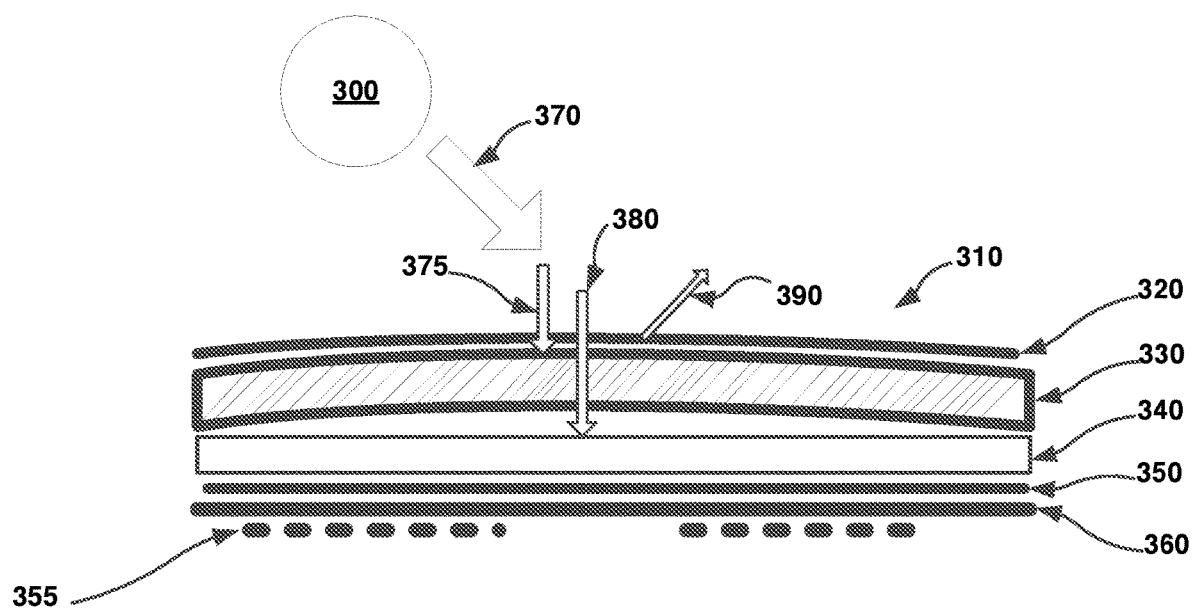
FIG. 3 is a conceptual diagram illustrating a cross-sectional view of the layers of the wearable head article, in accordance with one or more aspects of the present disclosure.

FIG. 3 is an illustration of a cross-sectional view of the wearable head article, e.g., baseball hat 10 of FIG. 1, and shows the different layers making up baseball hat 10, including a filter layer 330, outer material 320, baseball hat inner material 350, comfort layer 360. FIG. 3 may also include an optional protective layer, which, in some examples, may be the same as outer material 320 or the optional protective layer may be a separate layer that is separate from outer layer 320. FIG. 3 may also show how light 300, such as a light source, is affected by baseball hat 100 of FIG. 1, and may be natural such as the sun or artificial such as light bulb LED, laser, etc., shining on outer material 320, such as a light wave 370. When light wave 370 hits outer material 320 may allow beneficial light wavelengths 380 to pass through the optical filter 330. In this example, filter layer may be made up of optical filter 330 and optical converter 340, is at least one of an optical filter 330, an optical converter 340, which converts light wavelengths into therapeutic beneficial light wavelengths, and any combination thereof. Wavelengths of non-beneficial wavelengths 375 is harmful, non-beneficial, or both. Non-beneficial wavelengths 375 may be absorbed into optical filter 330 or reflected 390. In some examples, the optical filter 330 layer and the optical converter layer 340 are formed together in the same layer.

In another example of FIG. 3, the wearable head article the optical converter 340 may be made of material(s) employed for treating the target treatment area by blocking wavelengths present in natural sunlight 370 at least one of harmful wavelength 375 and/or non-beneficial wavelength (e.g. 375) to the individual, including, but not limited to, UV radiation, infrared radiation, wavelengths that promote a medical condition, are cell damaging, and are not useful for treating the medical condition.

FIG. 3 may also illustrate, in some examples, that the wearable head article, may further include a liner 360 disposed over the inner side of the wearable head article that improves air circulation, wherein liner 360 being formed from mesh, for allowing skin to breath. In other examples, padding or other comfort materials, air circulation materials, or heal control materials may be used for liner 360. In FIG. 3, there may also be an artificial light source 355, such as LEDs or other, attached to the inside of lining 360 near the target treatment area of the skin.

FIG. 3 is an example that may show filter layer 330, optical converter layer 340 and 320 are not adhesively bonded. In other examples, filter layer 330 (and possibly optical converter layer 340) may be adhesively bonded to the inner side of outer material 320. In other examples, filter layer 330, 320 may be made up of a plurality of panels forming a grid portion of the wearable head article for controlling the light at the target treatment area of the head.

In the illustrative example of FIG. 4, baseball hat 400 is a type of wearable head article that may include one or more sensor monitors for at least one of temperature, skin condition, light intensity, and wavelength of light spectral content.

FIG. 4 Baseball hat 400 may be an example of a wearable head article that further comprises a light means are attached to an inner side of the wearable head article in an array for emitting beneficial light within a treatment wavelength range. The system may include artificial lights, such as bill lights 420 for illuminating the face, and may also include or alternatively include scalp lights 440 for illuminating the scalp from the inner concave wall/side of the head portion of baseball hat 400. The system may also include sensors for sensing when a certain threshold temperature has been reached, such as bill sensor 460 and scalp sensor 480.

In one illustrative example, the array of lights may include red/infra-red option. This non-invasive, low-level and non-thermal light energy may be therapeutic for skin and may help tighten skin, minimize pores and improves the appearance of fine lines and wrinkles. In some examples, individuals may be able to manage their own treatments and touch ups at home or while traveling. The array of lights may operate with LED attachment heads or arrays of light of different light colors with different wavelengths. In another example, the array may contain a combination of lights that can emit light at different wavelengths.

The different wave lengths emitted by the array of lights may be therapeutic for different purposes. In one example, a red & infrared light may activate skin cells and accelerates the natural skin cell growth. This attachment head uses different light wavelengths that address the appearance of fine lines and wrinkles. In another example, a blue light may be added or alternative to the red/infra-red light and may be therapeutic for acne. It helps to combat acne causing bacteria, reduce inflammation and provide a rejuvenating effect on the skin. The blue light attachment addresses the underlying causes of acne. It helps to target acne causing bacteria, reduce puffiness and provide a rejuvenating effect on the skin. In another example, a green light therapy may be a non-irritating application for reducing hyper-pigmentation and age spots. All lights permeate the skins dermal layers to promote cell growth and rapid absorption of skin care products. The green light attachment may be formed from a non-irritating application for reducing hyper-pigmentation and age spots. Green light may also be used with moisturizers to improve hydration and effectiveness of the moisturizers.

Positioning of the arrays may also improve the effectiveness of the therapy. For example, red & infrared light may be positioned over or near the face and directed towards the face. The Red and Infrared light attachment or array may activate skin cells of the face and helps initiate and support collagen production. This device may use different light wavelengths that address the appearance of fine lines and wrinkles. In another example, green light may additionally or alternatively may be used because it is safe and effective for all skin types and offers light therapy for the skin. For example, when illuminating the face, neck or even the hands, the complexion may improve by tightening and reducing the size of pores, smoothing the skin's appearance. Green light may also reduce fine lines & dark spots.

A control 490 for a wearable head article that controls an array of lights attached to a wearable head article for treating skin conditions, comprising a programmable control means for controlling delivery of power to the array of lights, wherein the array of lights are located on an inner side of a filter layer, which allows a wearable head article for controlling light incident on the skin, including light to pass through a treatment area of the head, wherein the filer layer includes material that controls the wavelengths that pass through. Control 490 may be a handheld device, a smartphone, smart watch, tablet, FOB, computer, or any electronic device communicating with the components of baseball hat 400. Control 490 may receive data from components of baseball hat 400.

Control 490 may include programmable control means that may controls one or more of timing of power delivery to the array, duration of power delivery, strength of power delivery, power, delivery of power to a portion of the array of lights, a light wavelength for treatment, emitting light from the array at certain points targeting an area of the skin for treatment, receiving signals from at least one sensor, and other controls means.

Timers and/or electronic monitors can be employed to warn the user of excessive optical exposure to one or more areas of skin that are to be treated. In addition, electronic monitors can also provide additional information to the user including, but not limited to, general exposure conditions and conventional health conditions (e.g. pulse, body temperature, skin surface temperature, breathing). Feedback to the user can be by one or multiple means including audio alerts, visual alerts such as flashing lights and/or colored lights, communication to wearable electronic device/phone/tablet/computer/TV through bluetooth, wifi, etc.).

Furthermore, the hat/head covering/head gear can incorporate one or more electronic sensors which may provide feedback (including warnings) directly to the individual and/or at least one of phones, tablets, Amazon Alexa device, GOOGLE Home Hub device, Apple Hub device, Echo, Dot, watches, laptops and other computer devices using known communications means (audio, visual, blue tooth, WiFi, etc.). Dedicated applications can be implemented on the computing devices. Electronic sensors can measure one or more parameters including, but not limited to, the humidity, the temperature, the length of time the hat/head covering has been worn, the instantaneous and/or integrated irradiance (total and/or beneficial irradiance and/or harmful irradiance) to at least one specific area to be treated. Skin appearance and/or skin condition can be evaluated and reported. Therefore, the measured data can be recorded and stored locally and/or transmitted to a computer (including tablets, cellphones, watches, servers, GOOGLE Home Hub device, Apple Hub device, Echo, Dot, etc.) for storage and/or analysis. In one implementation electronic sensor(s) measure one or more parameters (e.g. the irradiance, integrated total irradiance) and issue a warning to the individual with the hat/head covering/head gear and/or a monitoring system. Warnings include, but are not limited to, excessive or too little total irradiance. The individual then can implement manual or electronic adjustments to the hat/head covering to correct the problem (or stop using the hat (for example, the integrated exposure limit has been reached or body temperature is too high, heart rate is problematic, etc.). For example, the electronic sensor(s) can correct the problem of excessive total irradiance by limiting or blocking (adjusting) the transmission of solar irradiance to at least one specific area of treatment to limit (e.g. over the specific area of treatment close or adjust holes or slits or apertures, slide an attenuating sheet of material, electronically-alter the attenuating properties of the transmissive material covering the specific area of treatment, etc.).

The electronics can be powered by power sources including, but not limited to, solar cells, batteries, capacitors, various energy-harvesting means, electromagnetic fields and electrical outlets. The power sources can be incorporated into the head covering/head gear or connected to the head covering/head gear by a wire/cable or through the open air.

A variation on the head covering/head gear that exploits beneficial natural sunlight wavelengths to promote head hair growth and/or to prevent/reduce head hair loss is a hybrid implementation that also incorporates one or more man-made (or artificial) beneficial light sources including, but not limited to, LED light sources emitting beneficial wavelengths to augment or compensate for deficiencies in the intensity of beneficial sunlight wavelengths incident on the skin. For example, GaAsP, AlGaInP, AlGaP and GaP are commercially-available LEDs that can be engineered to emit in red, orange, yellow and green parts of the visible spectrum. Other LEDs can incorporate appropriate phosphors or wavelength-shifting materials so as to emit in the beneficial wavelength range. The LED light sources could be manually activated or automatically activated based on sensor measurements. The LED beneficial light source(s) could be employed to enhance the rate of hair growth or slow the rate of hair loss in addition to the benefit derived from typical intensities of available beneficial natural sunlight wavelengths (augmentation) and/or to compensate for a deficiency when natural sunlight conditions are not adequate (reduced transmission due to angle-of-incident dependence of sunlight, clouds, fog, rain, reduced irradiance in the early morning or late afternoon, the night, when the sunlight is obstructed by an object or structure). The beneficial LED light can be distributed using one or more targeted distribution methods including, but not limited to, fiber optics/ light guides, diffusive screens, lenses, reflective surfaces. LEDs can be employed that emit light in a directional, a non-directional or a diffuse pattern. Additional artificial beneficial light sources (e.g. quantum dots, OLEDs, laser diodes) may be used in place of or in addition to LEDs. Artificial beneficial light sources may also include optical concentrators including various lenses and mirrors employed to collect and focus solar and/or artificial optical sources. These artificial beneficial light sources can be incorporated directly into the head cover/head gear or coupled to the head gear by optical means (e.g. fiber optics, light pipes, air). The previously described monitoring systems employing electronic sensors can be used to control (increase, decrease, turn off) and/or redirect the output of one or more of the artificial beneficial light sources.

An additional variation of the head covering/head gear implements only artificial (artificial) beneficial light sources in order to promote head hair growth and/or to prevent/ reduce head hair loss, forgoing the use of optical filter materials. These artificial beneficial light sources can be incorporated directly into the head cover/head gear or coupled to the head gear by optical means (e.g. fiber optics, light pipes, air, etc.) in order to irradiate the skin regions to be treated. The head covering/head gear incorporates an open grid structure that permits one or more artificial beneficial light sources to be mounted over a region of the head to be treated in order to encourage hair growth. The grid structure may incorporate absorptive and/or reflective materials to block the transmission of harmful wavelengths and optionally block transmission of non-beneficial wavelengths. The previously described monitoring systems employing electronic sensors can be used to control (increase, decrease, turn off) and/or redirect the output of one or more of the artificial beneficial light sources.

The hat/head covering/head gear can include various attachments including: cowls and visors incorporating at least one of optical filter materials, optical converter materials and covering materials for purposes of protecting and/or treating other areas of the face and neck. For example, blue (actually violet) LED light sources (approximate peak wavelengths in the range of 400-420 nm) are used to treat facial acne. A visor incorporates at least one of perforations, holes, slits, an aperture or apertures (windows) with optical filter materials to promote passage of preferred wavelengths (or wavelength bands) of light for treating facial areas with acne while blocking or significantly attenuating radiation wavelengths deemed harmful and optionally wavelengths determined to be non-beneficial. An optional second visor/glasses could protect the eyes as an alternative to wearing protective sunglasses. In one implementation electronic sensor(s) measure the integrated irradiance on the at least one facial area with acne and issue a warning to the individual with the visor and/or a monitoring system. In one implementation the individual wearing the head cover/head gear then can implement manual adjustments to the visor to correct the problem. In another implementation the electronic sensor(s) can correct the problem by adjusting the transmission of solar irradiance to at least one specific area of treatment to limit or block solar irradiance to the at least one facial area with acne. Furthermore, cowls incorporating properties detailed for visors can be employed to treat acne for areas of at least the neck and/or the upper back.

Furthermore, artificial beneficial blue (actually violet) emitting sources including, but not limited to, blue (violet) laser diodes, blue (violet) quantum dots, blue (violet) OLEDs, and blue (violet) LEDs (e.g. InGaN LEDs and optical sources used with optical concentrators) can be employed to enhance acne skin treatment in addition to the benefit from typical intensities of available beneficial blue-filtered sunlight wavelengths (augmentation) and/or be used to increase the intensity of beneficial blue-filtered (violet-filtered) wavelengths when natural sunlight conditions are inadequate (compensate for a deficiency). As previously described, a variety of means can be employed to deliver the blue (violet) beneficial light to the skin.

Figure 5:
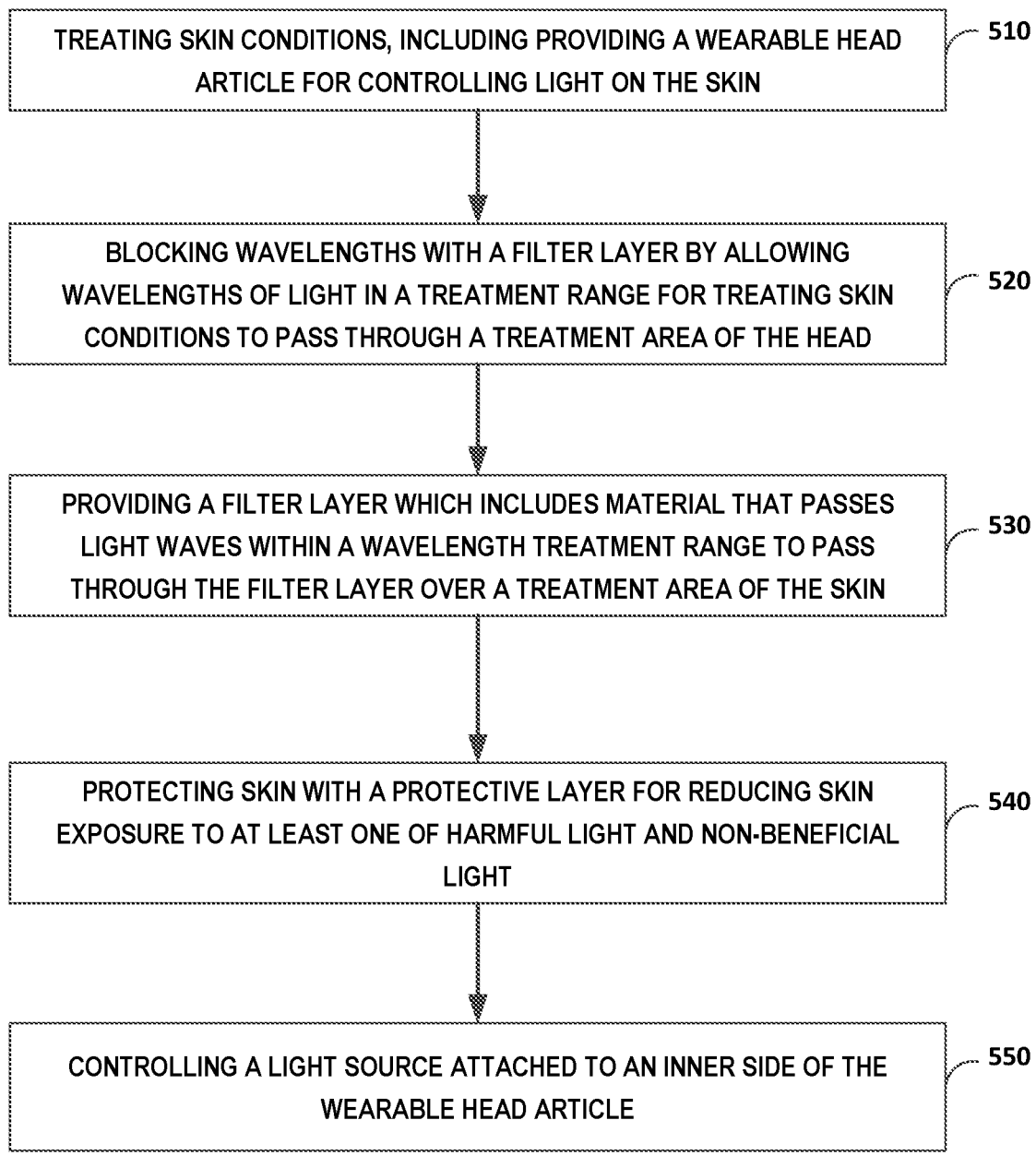
FIG. 5 is a block diagram illustrating an example of a method for filtering light from a wearable head article, in accordance with one or more aspects of the present disclosure.

FIG. 5 is a flow diagram that shows an example of a method for treating skin conditions for controlling light on the skin 510 in a wearable head article. The method may also include blocking wavelengths with a filter layer by allowing wavelengths of light in a treatment range for treating skin conditions to pass through over a treatment area of the head 520. Further in this method example, the filter layer may also include material that passes light waves within a wavelength treatment range over a treatment area of the skin 530; and protecting skin with a protective layer for reducing skin exposure to at least one of harmful light and non-beneficial light 540.

The method further including passing beneficial light wavelengths through the optical filter, converting light wavelengths by the optical converter into therapeutic beneficial light wavelengths, and any combination thereof. According to FIG. 5, the method may also include using an artificial light source. The artificial light source may include LEDs or other light creating sources. The artificial light source may be attached to the inner side of the wearable head article, for example the baseball hat as used throughout this disclosure and positioned on the inner side of the baseball hat, so that the inner side is the side nearest that wearer's scalp when worn. In other words, on the recessed inner side and controlling the light source attached to an inner side of the wearable head article 550. The artificial light source may be connected to a control, either remote or also located on the baseball hat, where the wearer of the baseball hat may control power to the artificial light source, strength of the lights, timing of the lights, patterns to each light emission, any combination thereof, or other control of the lights beneficial for treatment and safety of use of the lights.

While this invention has been described with reference to exemplary embodiments, it will be understood by those skilled in the art that various changes can be made and equivalents may be substituted without departing from the spirit and scope thereof. Modifications may also be made to adapt the teachings of the invention to particular problems, technologies, materials, applications and materials, without departing from the essential scope thereof. The invention is not limited to the particular examples that are disclosed herein, but encompasses all embodiments falling within the scope of the appended claims.

The invention is thus susceptible to various modifications and alternative forms, specific examples thereof having been shown by way of example in the drawings and described in detail. It is understood that the invention is not limited to the particular forms or methods disclosed, but to the contrary, the invention encompasses all modifications, equivalents, and alternatives falling within the spirit and scope of the claims.

What is claimed is:

1. A wearable head article, for controlling light incident, arranged in a grid structure, wherein the grid structure is configured to have at least one grid portion, which includes layers, wherein the at least one grid portion is configured in the wearable head article to target an area of skin for treatment, the layers of the at least one grid portion include:
    at least one filter layer for blocking at least one of harmful and non-beneficial light incident, based on filter layer material of each respective layer of the portion of the grid structure, wherein each of the respective filtering grid portions includes at least one filter layer for blocking at least one of harmful and non-beneficial light incident, based on material of each of the respective layers, wherein the respective filter layer blocks at least one of harmful and non-beneficial wavelengths of the light passing through the filter layer material attached to the grid structure at the portion and configured to pass the at least one wavelength to treat an area of skin; and
    a protective layer, different from the at least one filtering grid portion of the grid structure, for reducing skin exposure to at least one of harmful light and non-beneficial light.

2. The wearable head article of claim 1, wherein the filter layer includes at least a harmful UV light blocking material.

3. The wearable head article of claim 1, wherein the head article is at least one of a hat, a helmet, visor, bandana, scarf, headband, earphones, yarmulke, a hajib, mask, bonnet, hood, and any combination thereof.

4. The wearable head article of claim 1, wherein the filter layer is located in at least a portion of the wearable head article near the treatment area of the head for treating the skin for treatments within a target range, treating medical conditions, including, but not limited to, hair loss, psoriasis, fungus, acne, rosacea, wrinkles/aging, capillaries, bruising, sunburns, bacterial infections, insomnia and depression, and for treatment of the skin for collagen support, repair and growth, and cellular rejuvenation and regeneration.

5. The wearable head article of claim 1, wherein the filter layer is at least one of an optical filter, which allows beneficial light wavelengths to pass through the optical filter, an optical converter, which blocks at least some harmful and non-beneficial light wavelengths into therapeutic beneficial light wavelengths, and any combination thereof.

6. The wearable head article of claim 1, wherein the filter layer is removeable formed of optical blocking materials, wherein the grid structure is configured to receive, by the portion of the grid structure, an insert of the filter layer with a different filter layer.

7. The wearable head article of claim 1, wherein the filter layer optical converter material(s) employed for treating the target treatment area block wavelengths present in natural sunlight at least one of harmful and non-beneficial to the individual, including, but not limited to, UV radiation, infrared radiation, wavelengths that promote a medical condition, are cell damaging, and are not useful for treating the medical condition.

8. The wearable head article of claim 1, further including a liner attached to at least one of the filter layer, the protective layer, and a combination thereof, and disposed over the inner side of the wearable head article that improves air circulation, wherein the liner being formed from mesh, for allowing skin to breath.

9. The wearable head article of claim 1, wherein the filter layer of filter material is a piece of flexible film.

10. The wearable head article of claim 1, further comprising a band extending circumferentially around the bottom of the hat, and a brim or bill extending out from the band, wherein the brim or bill of the wearable article contains the filter layer material for treating skin conditions on the face.

11. The wearable head article of claim 1, wherein the filter layer and the protective layer are formed together in the same layer.

12. The wearable head article of claim 1, wherein the filter layer is formed of light filtering film material in a panel form for inserting the panel in the wearable head article near the target treatment area.

13. The wearable head article of claim 1, wherein the filter layer is formed in a shape removably fitting into a pocket portion of the wearable head article.

14. The wearable head article of claim 1, wherein the filter layer is adhesively bonded to the wearable article.

15. The wearable head article of claim 1, wherein the filter layer is a plurality of panels forming a grid portion of the wearable head article for controlling the light at the target treatment area of the head, wherein the plurality of panels are removeable and the wearable head article is configured to receive the filter layer of the at least one of the Plurality of panels that form the at least one grid portion.

16. The wearable head article of claim 1, wherein a sensor monitors for at least one of temperature, skin condition, light intensity of an array of lights attached to the protective layer, and light spectral content.

17. The wearable head article of claim 1, wherein the filter layer is an optical filter, which allows beneficial light wavelengths to pass through the optical filter, and the grid structure further includes at least one of an optical converter, which converts at least one of harmful and non-beneficial light wavelengths into therapeutic beneficial light wavelengths, and light emitting diode lights attached to the grid structure for providing additional beneficial light.

18. A method for using a wearable head article for treating skin conditions including:

providing the wearable head article, for blocking light, arranged in a grid structure, which includes at least one grid portion configured for targeting an area of skin for treatment, wherein the at least one grid portion includes at least one filter layer;

blocking at least one of harmful and non-beneficial wavelengths with the at least one filter layer, based on filter layer material of each respective layer of the portion of the grid structure, wherein each of the respective filtering grid portions includes at least one filter layer for blocking at least one of harmful and non-beneficial light incident, based on material of each of the respective layers, wherein the respective filter layer controls at least one wavelength of the light passing through the filter layer material attached to the grid structure at the portion and configured to pass the at least one wavelength to treat an area of skin; and protecting skin with a protective layer, different from the at least one filtering portion of the grid structure, for reducing skin exposure to at least one of harmful light and non-beneficial light.

19. The method of claim 18, further including passing beneficial light wavelengths through the optical filter, converting at least some of harmful and non-beneficial light wavelengths by the optical converter into therapeutic beneficial light wavelengths, and any combination thereof.

\* \* \* \* \*